US009561083B2

(12) United States Patent
Yu et al.

(10) Patent No.: US 9,561,083 B2
(45) Date of Patent: Feb. 7, 2017

(54) ARTICULATING FLEXIBLE ENDOSCOPIC TOOL WITH ROLL CAPABILITIES

(71) Applicant: Auris Surgical Robotics, Inc., San Carlos, CA (US)

(72) Inventors: Alan Yu, Union City, CA (US); Jason Lee, Milpitas, CA (US)

(73) Assignee: Auris Surgical Robotics, Inc., San Carlos, CA (US)

( * ) Notice: Subject to any disclaimer, the term of this patent is extended or adjusted under 35 U.S.C. 154(b) by 0 days.

(21) Appl. No.: 15/072,072

(22) Filed: Mar. 16, 2016

(65) Prior Publication Data

US 2016/0270866 A1    Sep. 22, 2016

Related U.S. Application Data

(60) Provisional application No. 62/134,366, filed on Mar. 17, 2015.

(51) Int. Cl.
*A61B 34/30* (2016.01)
*A61B 17/00* (2006.01)

(52) U.S. Cl.
CPC ........ *A61B 34/30* (2016.02); *A61B 2017/0034* (2013.01); *A61B 2017/00323* (2013.01); *A61B 2034/301* (2016.02); *A61B 2034/303* (2016.02)

(58) Field of Classification Search
CPC ..................... A61B 34/30; A61B 2017/00323; A61B 2017/0034; A61B 2034/303; A61B 2034/301
See application file for complete search history.

(56) References Cited

U.S. PATENT DOCUMENTS

| | | | |
|---|---|---|---|
| 3,892,228 | A | 7/1975 | Mitsui |
| 7,771,416 | B2 | 8/2010 | Spivey et al. |
| 8,911,471 | B2 | 12/2014 | Spivey et al. |
| 2012/0143226 | A1* | 6/2012 | Belson ............... A61B 17/0057 606/148 |
| 2013/0197556 | A1 | 8/2013 | Shelton, IV et al. |
| 2014/0251042 | A1 | 9/2014 | Asselin et al. |
| 2015/0032151 | A1 | 1/2015 | Ishida et al. |
| 2016/0001038 | A1 | 1/2016 | Romo et al. |

\* cited by examiner

*Primary Examiner* — Theodore Stigell
*Assistant Examiner* — Amber Stiles
(74) *Attorney, Agent, or Firm* — Wilson, Sonsini, Goodrich & Rosati

(57) ABSTRACT

Instrument device with an elongated, flexible shaft that is configured to both roll and articulate in a controllable manner. The claimed system and apparatus provides endoscopic rolling and articulating capabilities with minimal tradeoffs in control, allowing for greater ease of use and clinical efficacy.

30 Claims, 14 Drawing Sheets

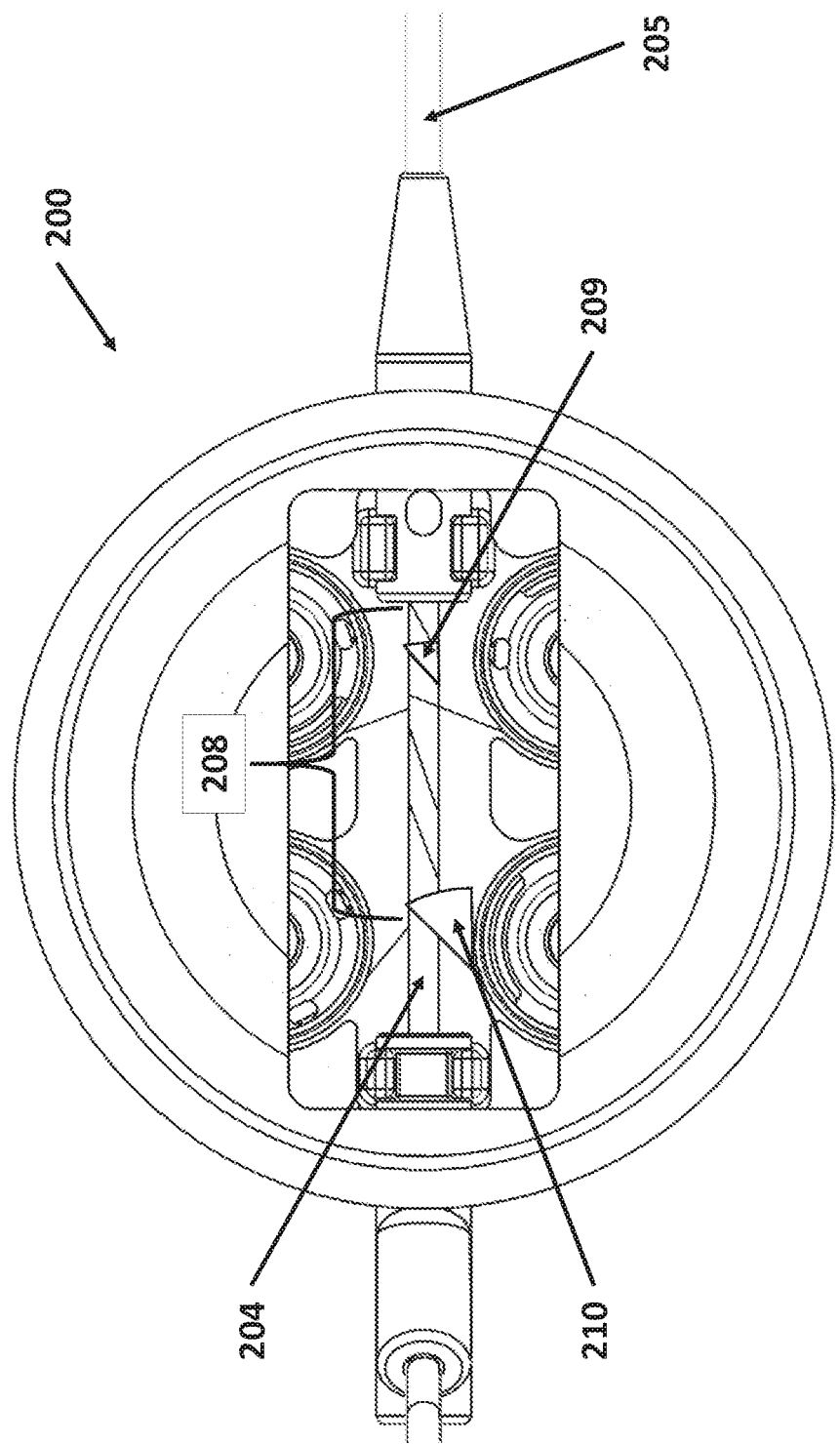

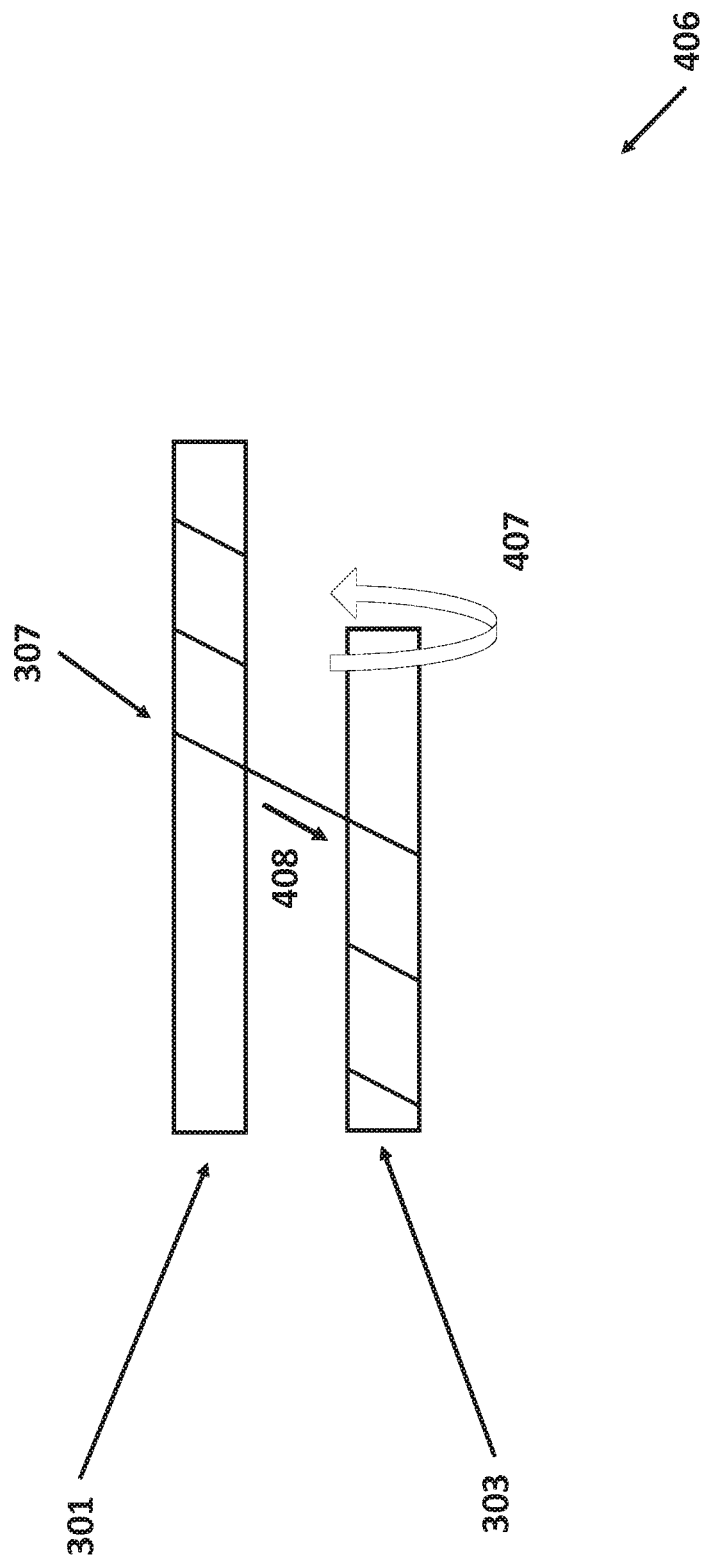

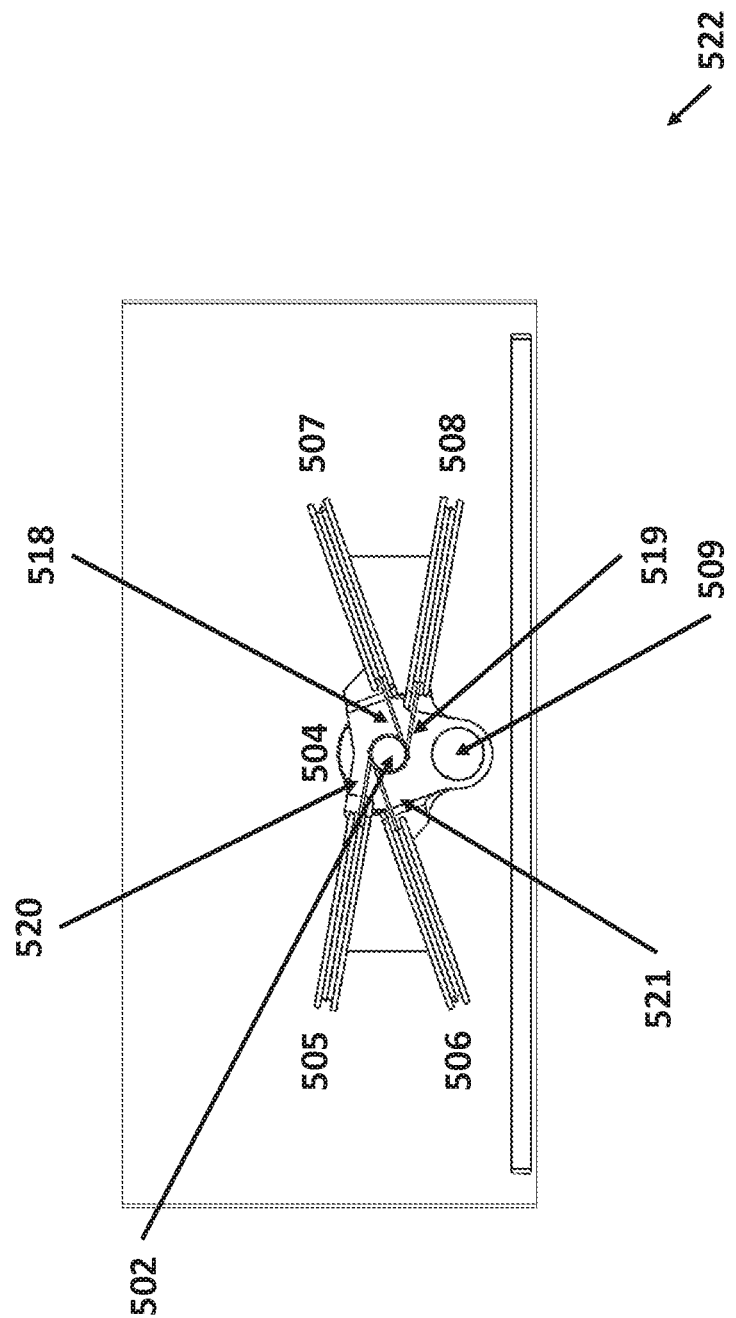

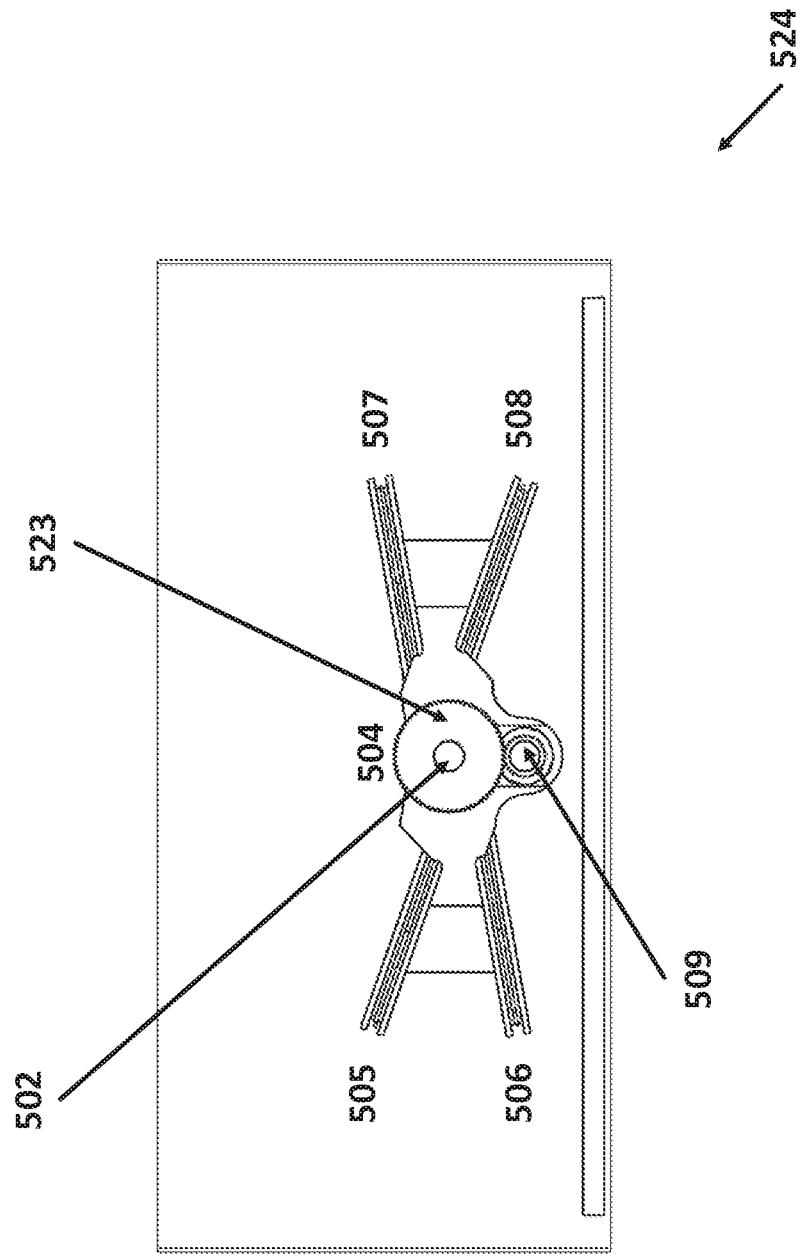

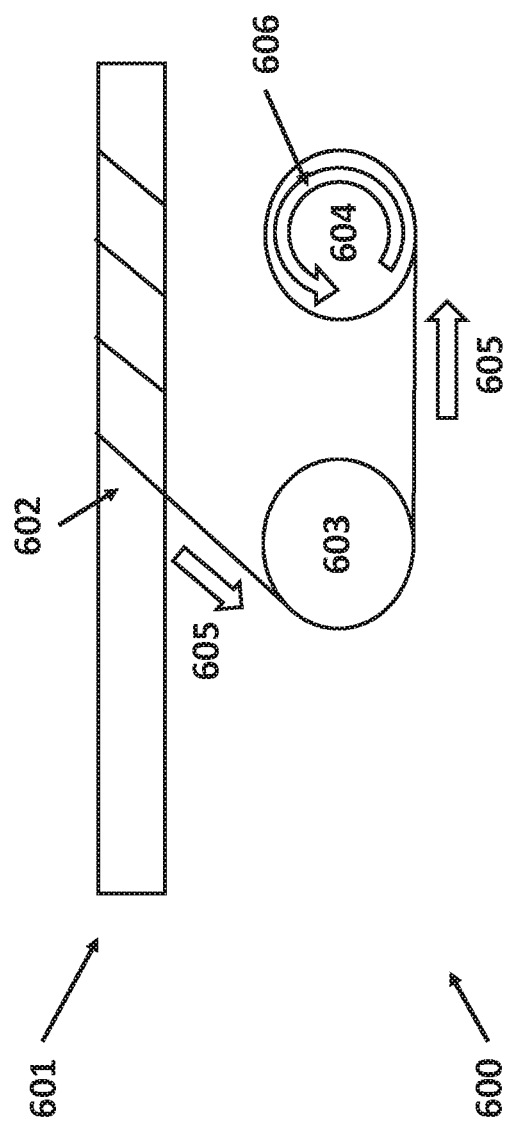

ARTICULATING FLEXIBLE ENDOSCOPIC TOOL WITH ROLL CAPABILITIES

CROSS-REFERENCE

This application claims the benefit of U.S. Provisional Application No. 62/134,366, filed Mar. 17, 2015, which application is incorporated herein by reference.

The present invention relates to medical instruments, tools, and methods that may be incorporated into a robotic system, such as those disclosed in U.S. patent application Ser. No. 14/523,760, filed Oct. 24, 2014, U.S. Provisional Patent Application No. 62/019,816, filed Jul. 1, 2014, U.S. Provisional Patent Application No. 62/037,520, filed Aug. 14, 2014, and U.S. Provisional Patent Application No. 62/057,936, filed Sep. 30, 2014, the entire contents of which are incorporated herein by reference.

BACKGROUND OF THE INVENTION

1. Field of the Invention

The field of the present invention relates to flexible endoscopic tools that may be used in a number of endolumenal procedures. More particularly, the field of the invention pertains to flexible endoscopic tools that have roll capabilities for use during endolumenal procedures.

2. Description of the Background Art

The spread of robotic surgery has precipitated the development of novel technologies. For example, in order to enable a robotically-driven endoscopes, robotically-driven tools are more useful when they are able to both articulate in a desired linear direction and roll in a desired angular direction. In current elongated medical devices, roll in the device shafts is often achieved at the expense of pull-cable management. For example, in some laparoscopic devices on the market, roll of the rigid shaft may be accomplished by simply twisting the actuation pull wires (used for manipulation of the device's end effectors and/or wrist) around each other at the same rate as the shaft. Due to mechanically-limited revolutions in either direction, the twist in the cables show little to no adverse effect on either roll or grasper manipulation. Nevertheless, this lack of pull-wire management results in noticeably varying levels of friction throughout the shaft rotations. The accumulated friction steadily increases with each rotation until the pull wires are tightly bound around one another.

FIG. 1 illustrates the physical limitations of current elongated devices arising from the implementation of roll capabilities. Specifically, FIG. 1 illustrates how the implementation of roll capabilities in a prior art device creates undesirable friction and winding of the articulation pull wires. As shown in FIG. 1, the pull wires 104 in prior art device 100 extend from the distal tip 102 and at the proximal end 101 of the device 100. Rotation of the shaft 103 forces the pull wires 104 to twist amongst one another along the entire length of the hollow shaft 103. As the shaft 103 rotates beyond a full rotation, the tensioned wires start to tightly wrap around one another much like a wire-rope. Eventually, the pull-wires 104 would not be able to overcome the resulting friction to exert tension on the elements on the distal end 102.

In competing products, such as the TransEnterix SurgiBot, articulation and roll are de-coupled using a robotic outer "sheath" to enable pitch and yaw articulation, while a flexible laparoscopic tool controls insertion roll and end-effector actuation. However, this results in an unnecessarily large system with two separate modules controlling different degrees of freedom. Separate modules complicate the pre-operative workflow because the operator must now register two sets of devices relative to the patient.

In manual endoscopes, knobs and dials actuate the distal tip of the scope while rotation of the shaft is achieved by twisting the entire proximal end of the tool. As a result, when rolling the scope, the operator is forced to contort into an uncomfortable, compensatory position in order to operate the knobs and dials. These contortions are undesirable; thus, necessitating a different approach.

Accordingly, there is a need for an endoscopic tool that is capable of rolling without compromise to its actuation and articulation capabilities, while also being ergonomically ease to use.

SUMMARY OF THE INVENTION

In general, the present invention provides a flexible endoscopic tool that has both articulation and roll capabilities. In one aspect, the present invention provides for a medical instrument comprising an elongated member, and an instrument base located at the proximal end of the elongated member, the base comprising a pull wire configured to spiral along the shaft at a helical pitch and a helical angle, and a translating redirect member configured to direct the pull wire to begin spiraling along the elongated member at a consistent angular position on the elongated member.

In another aspect, the instrument base further comprises a lead screw configured to longitudinally translate the redirect member relative to the elongated member in response to rotating the lead screw. In another aspect, the lead screw is further configured to roll the elongated member. In another aspect, longitudinal translation of the redirect member relative to the shaft maintains the helical pitch of the pull wire around the shaft it rolls. In another aspect, longitudinal translation of the redirect member relative to the shaft maintains the helical angle of the pull wire around the shaft it rolls.

In yet another aspect, the medical instrument further comprises a rotatable spool configured to rotate in response to longitudinal translation by the redirect member. In another aspect, the spool rotates in order to either collect or pull wire length. In another aspect, the lead screw is coupled to a transmission gear that is configured to transmit angular motion from the lead screw to the elongated member.

BRIEF DESCRIPTION OF THE DRAWINGS

The invention will be described, by way of example, and with reference to the accompanying diagrammatic drawings, in which:

FIGS. 2A-2C illustrates the physical limitations arising from use of a central shaft to capture the winding pull wires arising from rotations, in accordance with an embodiment of the present invention;

FIGS. 4A-4B illustrates how the helical angle of the pull wire wrap around the elongated shaft may be controlled by rolling the articulation shaft in concert with rolling the elongated shaft, in accordance with an embodiment of the present invention;

FIG. 5B illustrates a frontal view of idler carriage 504 and elongated shaft 502 in endoscopic device 501 from FIG. 5A;

FIG. 5D illustrates a rear view of the elongated shaft idler carriage FIGS. 5A, 5B and 5C;

FIG. 6A illustrates how a single pull wire may be tensioned in order to generate articulation in the elongated shaft;

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

In clinical applications, the design of the instrument base, which includes the robotic interface and the mechanical assembly to enable articulation and roll, is often constrained in size and design. For example, in a robotically-driven system, the design of the instrument base may be limited by both the lifting power of the robotic appendages and the necessity of maintaining a sterile barrier. Moreover, the use of pull wires to actuate the endoscopic shaft further complicates attempts to implement roll into the endoscopic shaft design.

Accordingly, the present invention provides an efficient, compact design for a robotically-driven tool that accomplishes both articulation and roll in its shaft with minimal design compromises.

Figure 1:
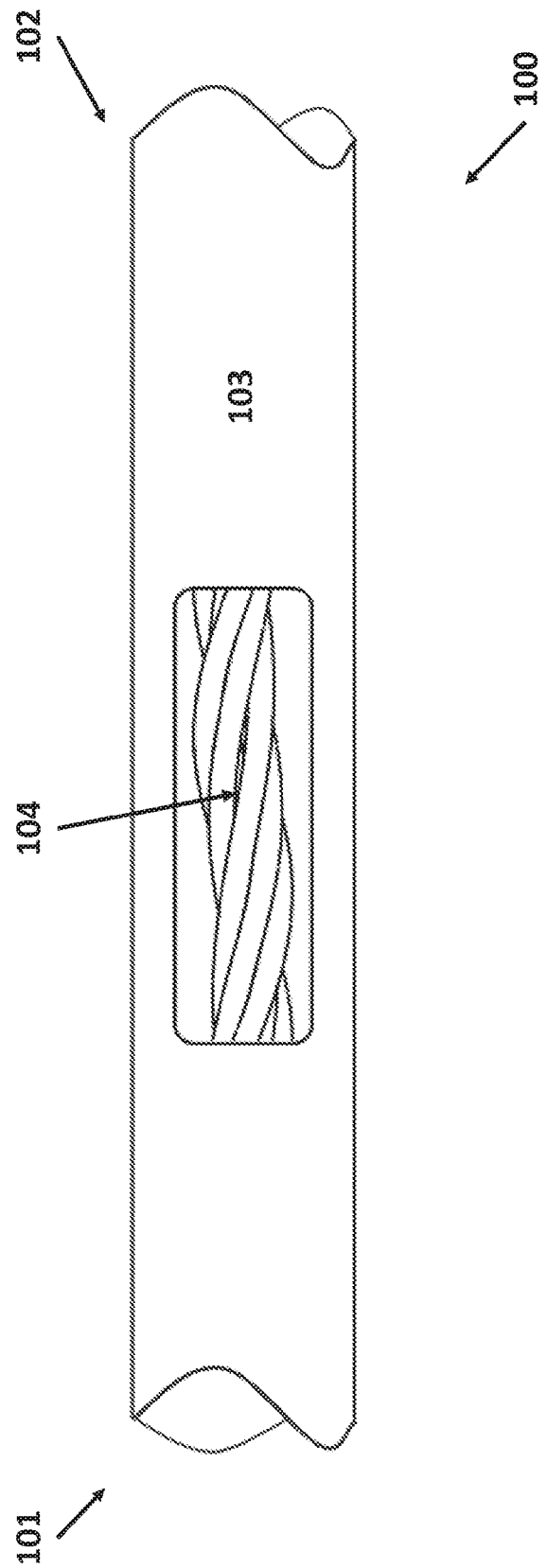
FIG. 1 illustrates the physical limitations in current elongated devices arising from the implementation of roll capabilities, consistent with the current state of the art.
Figure 2A:
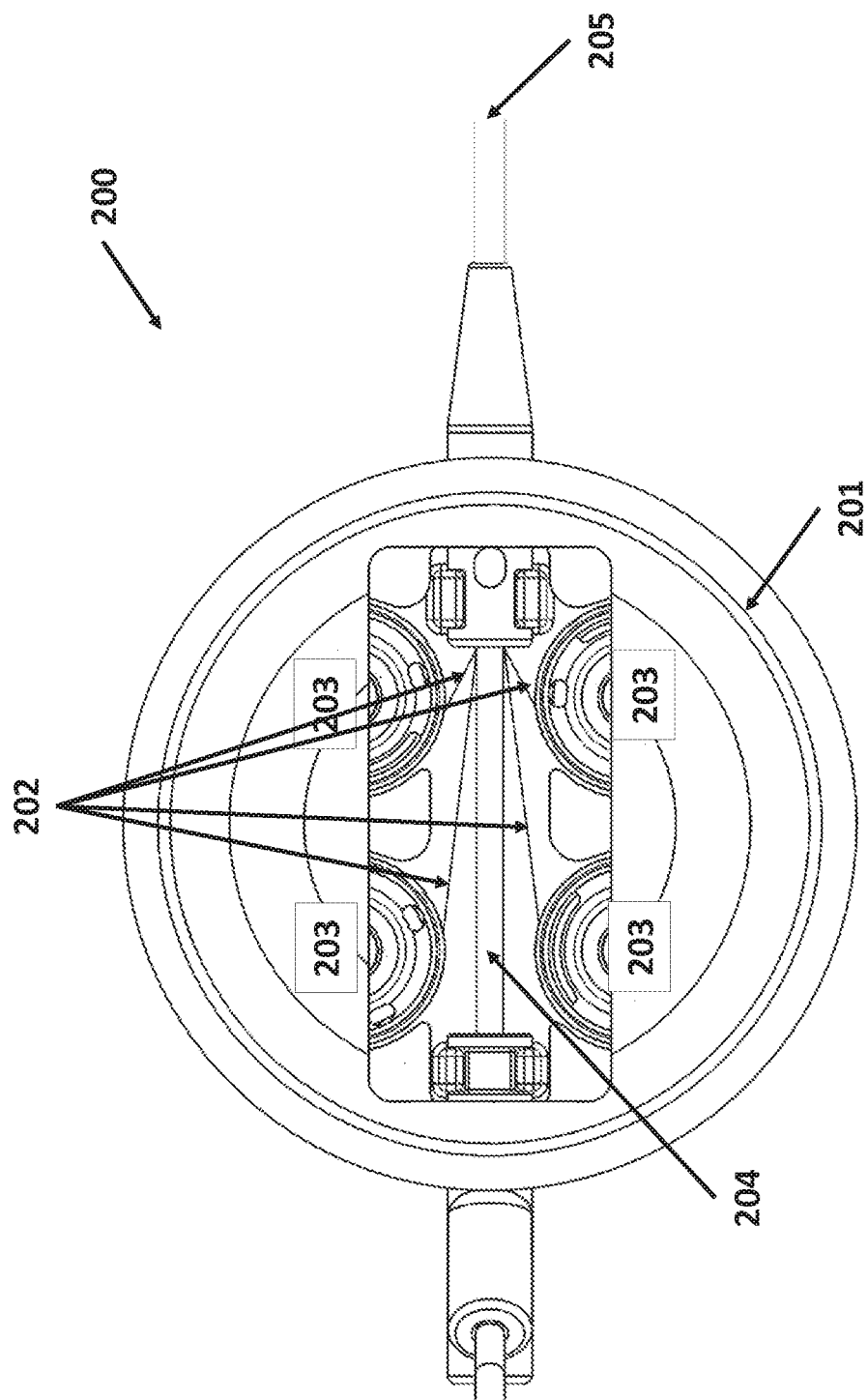
Figure 2B:
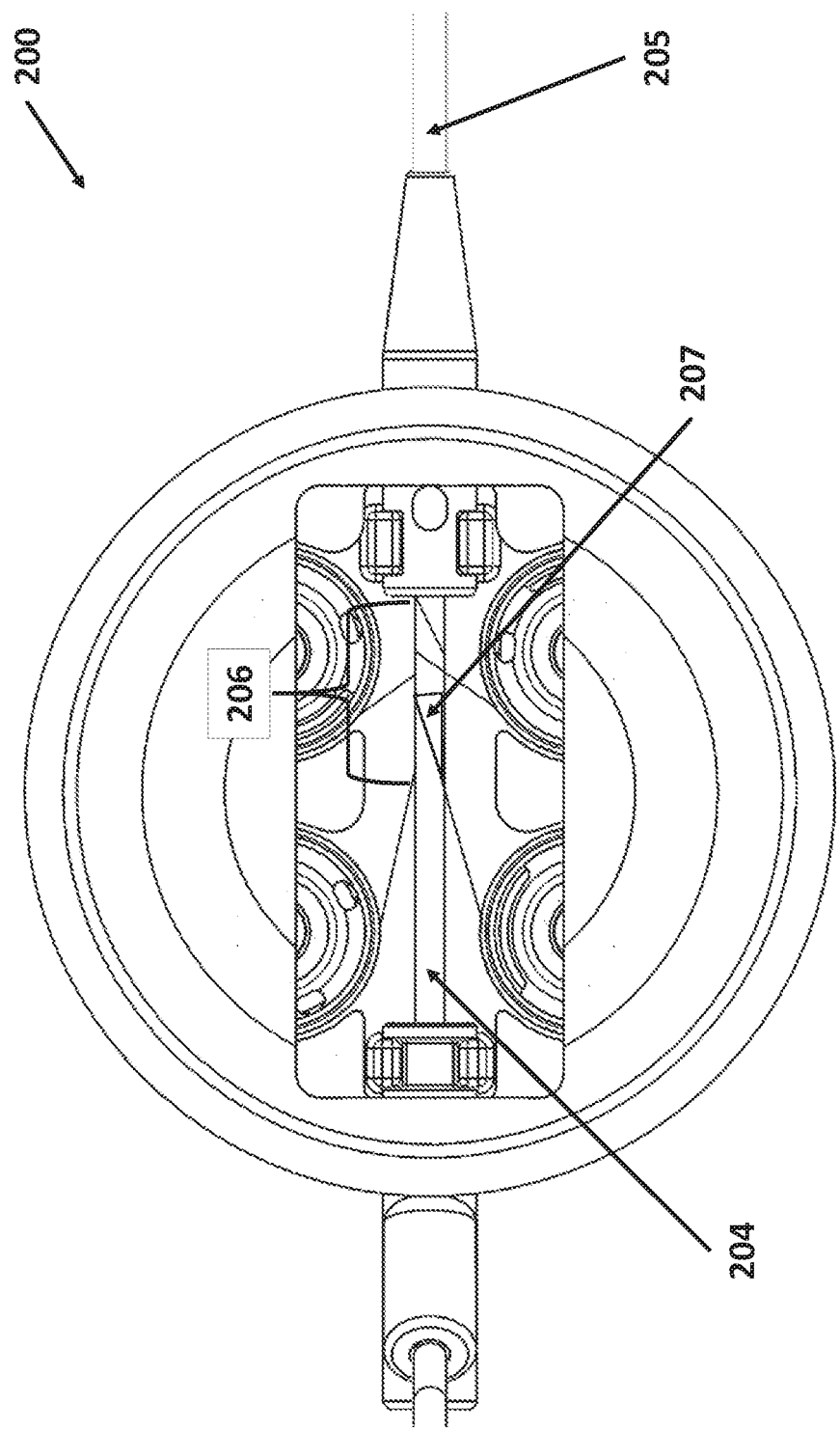

An improvement on current devices, use of an internal shaft within the elongated shaft may be used to interrupt the wire-on-wire wrapping by introducing a low-friction surface upon which the wire can wrap around. Merely adding an internal shaft to the current art, however, creates a number of engineering challenges. FIGS. 2A-2C illustrates the physical limitations arising from use of a central shaft to capture the winding pull wires arising from rotations, in accordance with an embodiment of the present invention. In FIG. 2A, the device 200 remains at rest with respect to roll, revealing that the pull wires 202 within the instrument base 201 in device 200 extend from the spools 203 to the distal end of the internal shaft 204. The outer shaft 205 is configured with a concentrically aligned internal shaft 204 that is designed to act as a low-friction surface upon which the wires may wrap around.

In FIG. 2B, the outer shaft 205 has been slightly rotated, resulting in the pull wires 202 winding around the internal shaft 204. The pull wire 202 winding and twisting around internal shaft 204 results in the pull wires 202 spiraling into a wrap 206 around the internal shaft 204 at particular helical angle 207 and helical pitch as the outer shaft 205 rolls.

In FIG. 2C, the outer shaft 205 has been heavily rotated, resulting the pull wires 202 further winding around the internal shaft 204. As the outer shaft 205 is rotated, the pull wires 202 "crawl" along the internal shaft 204 in order to compensate for their changed angular position with respect to the internal shaft 204. The resulting wrap 208 of the pull wires 202, however, causes the helical angle 209 of the wrap 208 to grow progressively aggressive, i.e., the helical angles of the wrap 208 grow steeper and steeper relative to the internal shaft 204.

The change in the helical angles of wrap 208 are largely the result of the changing "takeoff angle" 210, i.e., the angle at which the pull wires 202 begin to wrap around the internal shaft 204, as the external shaft 205 rolls. As the internal shaft 204 rotates, the static position of the spools 202 relative to internal shaft 204 and wrap 208 creates a steeper and steeper takeoff angle 210 as the wrap 208 crawls along the internal shaft 204. Additionally, since the spools are at different locations relative to the wrap 208, the takeoff angles at each spool may be different. At the extreme, the wrap 208 around the internal shaft 204 would lock due to friction, a phenomenon that reflects Capstan's principle, wherein the helical pitch 209 would be orthogonal to the internal shaft 204, resulting in the wrap 208 completely wrapping about itself, i.e., where the helical pitch would be zero. At that point, the pull-wire 202 would not be able to overcome the friction and serve its purpose.

The "crawl" of the wrap 208 also transmits tension in the pull wires 202. When pull wires are used in flexible devices, such as catheters, the resulting tension from roll is undesirable and can lead to shaft compression, unwanted stiffness, and hindered steering performance. Moreover, the resulting tension is non-linear and unpredictable, leading to an unpredictable mathematical model for controlling the device. Given that a changing helical angle and helical pitch creates controls and engineering challenges, additional embodiments are needed that incorporate internal shaft roll mechanisms to accommodate.

Figure 3:
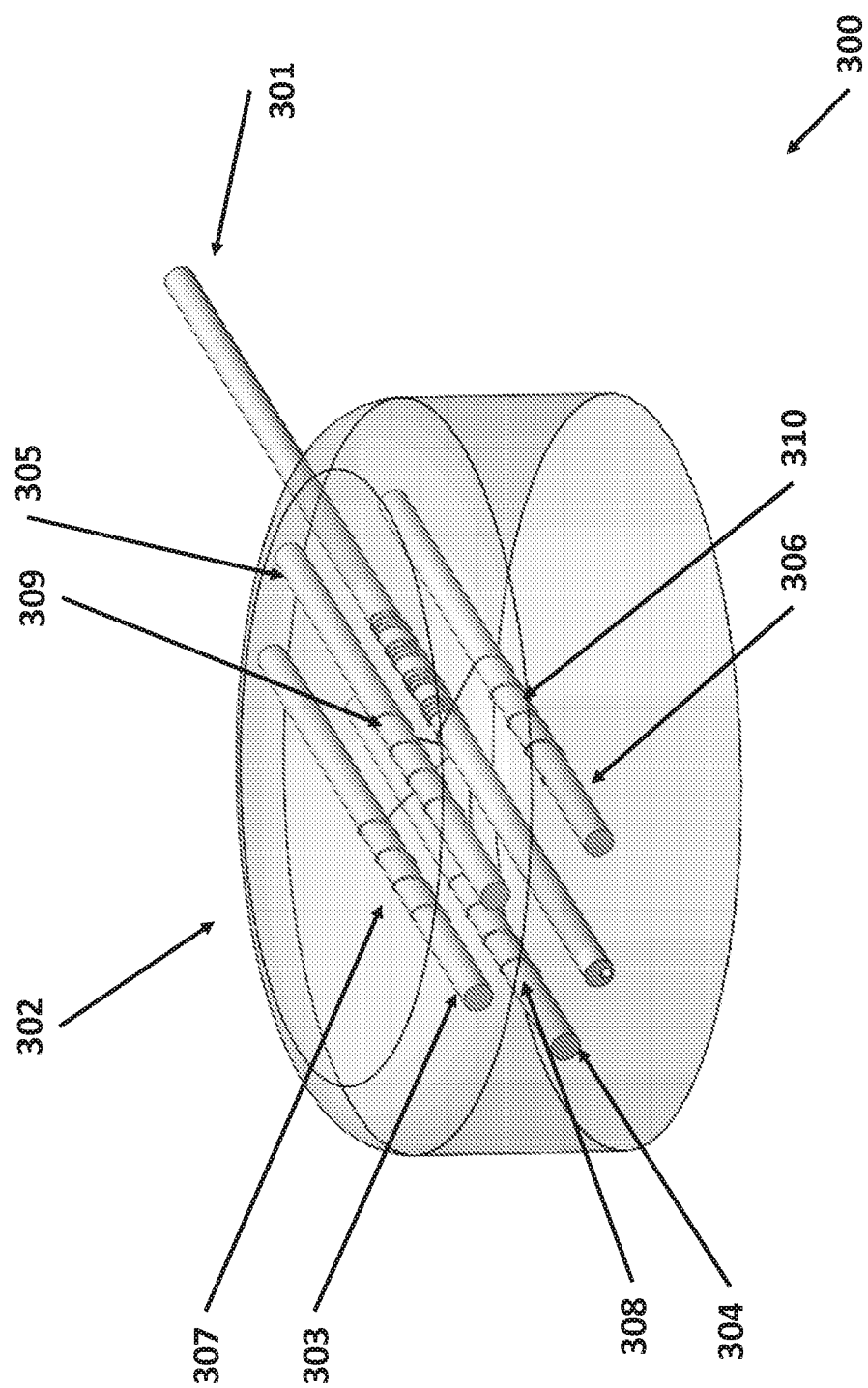
FIG. 3 illustrates an endoscopic device with an instrument base comprising multiple rolling structures, in accordance with an embodiment of the present invention.

FIG. 3 illustrates an endoscopic device with an instrument base comprising multiple rolling structures, in accordance with an embodiment of the present invention. In FIG. 3, the device 300 comprises an elongated shaft 301 and instrument base 302. The instrument base 302 comprises four articulation shafts 303, 304, 305, and 306 that act as redirect surfaces for pull wires 307, 308, 309, and 310 respectively. Each of the aforementioned pull wires are wrapped in spiral fashion around their respective articulation shafts before being wrapped in spiral fashion around the elongated shaft 301.

Figure 4A:
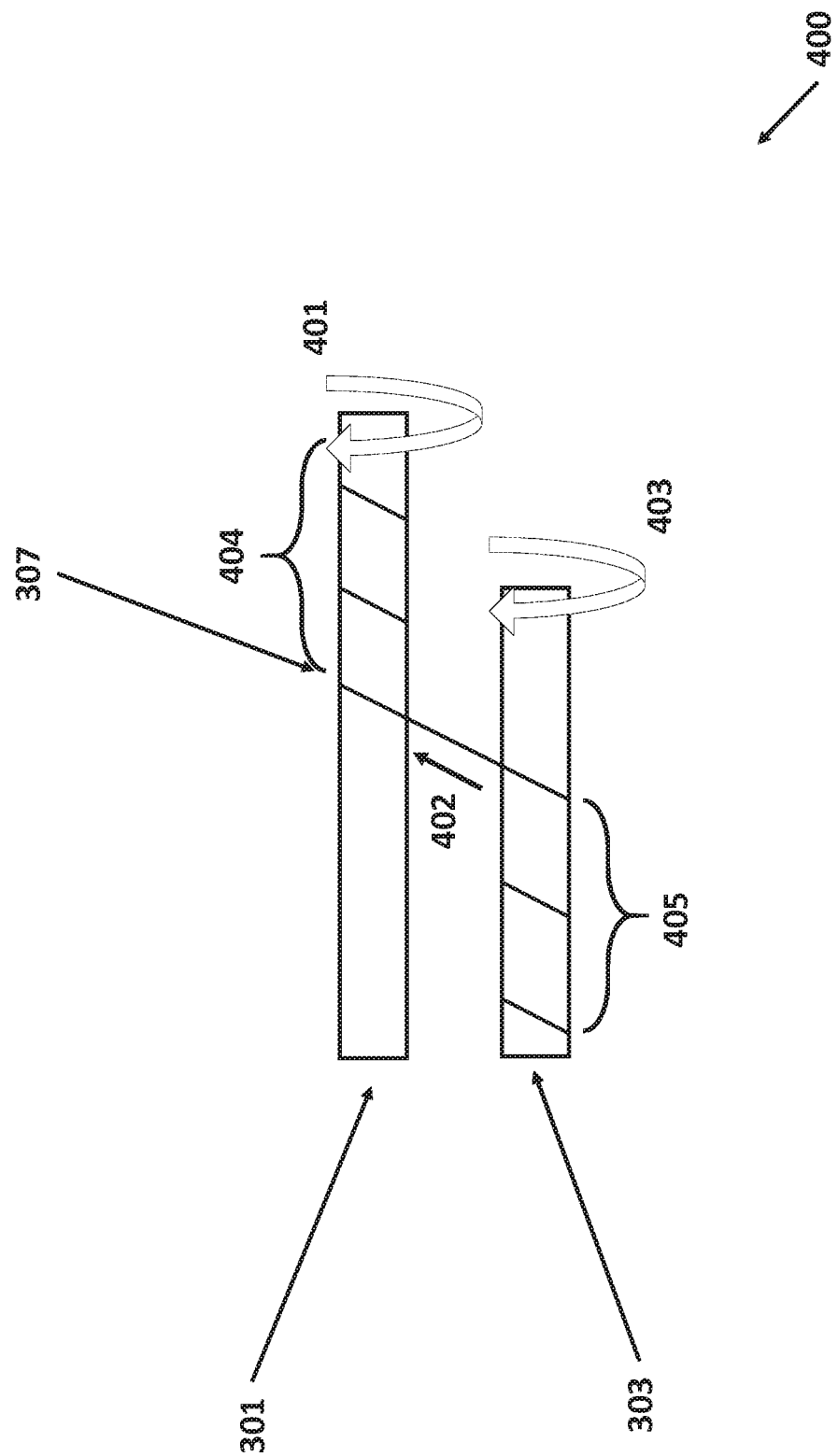

The use of parallel articulation shafts provides for controlled wrapping of the pull wires around the elongated shaft due to roll by coordinating roll among the articulation shafts. FIGS. 4A-4B illustrates how the helical angle of the pull wire wrap around the elongated shaft may be controlled by rolling the articulation shaft in concert with rolling the elongated shaft, in accordance with an embodiment of the present invention. Specifically, FIG. 4A illustrates how roll of the elongated shaft 301 from device 300 may be accomplished without creating an unstable helical pitch and angle and undesirable tension. In FIG. 4A, view 400 isolates and focuses on pull wire 307 wrapped around both articulation shaft 303 and elongated shaft 301 within instrument base 302 of device 300 from FIG. 3. When elongated shaft 301 is rolled in the direction shown by arrow 401, in the absence of any corresponding roll in articulation shaft 303, undesirable tension 402 would result in pull wire 307. Accordingly, to compensate for that rise in tension 402, articulation shaft 303 may be rolled in the (same) direction as the elongated shaft 301 as shown by arrow 403. In effect, as the elongated shaft 301 "wraps" up the pull wire 307, additional length of pull wire 307 is "unwrapped" from articulation shaft 303. When the rate of roll 401 and 403 are matched, there is no tension or slack in the pull wire 307. This ensures that the helical pitch and angle of the wrap 404 on elongated shaft 301 and the helical pitch and angle of the wrap 405 on the articulation shaft 303 is consistent and predictable. This results in a linear mathematical model for calculating control of the pull wire 307.

FIG. 4B illustrates how tension on pull wire 307 may be generated by rolling the articulation shaft 303 relative to the elongated shaft 301, in accordance with an embodiment of the present invention. In FIG. 4B, view 406 shows rotation of the articulation shaft 303 in the direction indicated by arrow 407. If elongated shaft 301 rolls at a slower rate in the same direction, rolls in the opposite direction, or is held in place rotationally, pull wire 307 will experience tension in the direction indicated by arrow 408. Accordingly, tension along the pull wire 307 convey axial compression force down the elongated shaft 301 of the device, resulting in articulation of the device. In circumstances when used in combination with an end effector, the axial compression results in actuation of the end effector element.

As shown in FIGS. 4A and 4B, providing secondary structures that assist with the wrap may accommodate the wrapping of the pull wires around the central shaft. The coordinated rolling of both the elongated shaft 301 in combination with the articulation shaft 303, which wraps pull wires at a precise helical pitch and angle, allows for a consistent helical pitch and angle on the elongated shaft 301, regardless of whether the operator desires roll in the elongated shaft 301 or tension in the pull wires. In practice, maintaining a consistent helical pitch generally results in a consistent helical angle.

While embodiments with multiple rolling structures resolve several of the design challenges arising from incorporating articulation and roll, in practice, the use of multiple rolling structures may create issues when attempting to interface the instrument with the robotic drive mechanism.

Figure 5A:
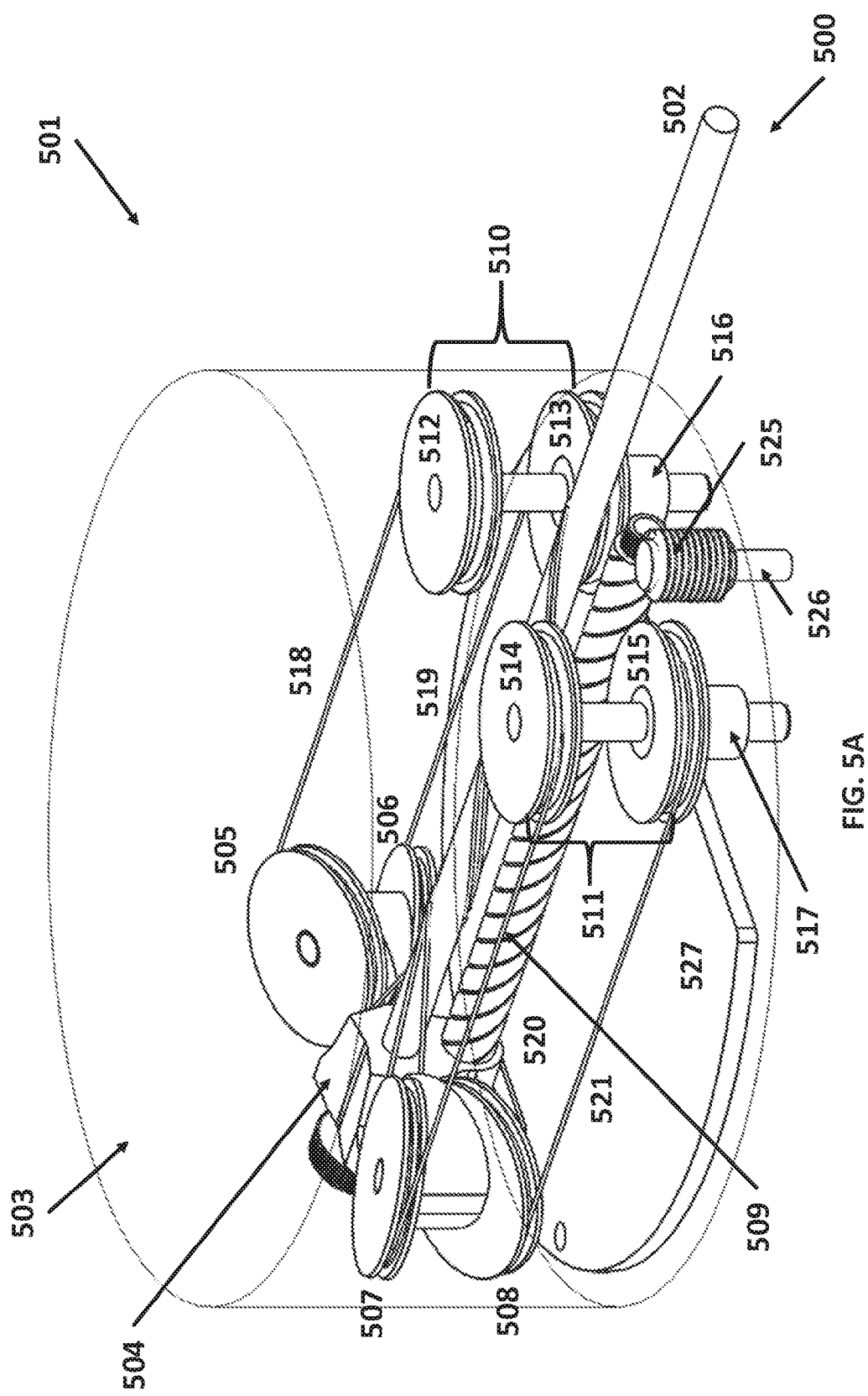
FIG. 5A illustrates an endoscopic device with an instrument base that utilizes a lead screw and angled idlers to ensure a consistent helical pitch around an elongated shaft, in accordance with an embodiment of the present invention.

FIG. 5A illustrates an endoscopic device with an instrument base that utilizes a lead screw and angled idlers to ensure a consistent helical angle and pitch around an elongated shaft, in accordance with an embodiment of the present invention. As shown in isometric transparent view 500, endoscopic device 501 principally comprises an elongated shaft 502 and an instrument base 503. Within instrument base 503, an idler carriage 504 is disposed along the elongated shaft 502, and configured to longitudinally translate and slide along the elongated shaft 502.

The idler carriage 504 holds four angled idlers 505, 506, 507, and 508 at a fixed angle relative to the elongated shaft 502. The angle of the angled idlers may be chosen for a particular purpose. FIG. 5B illustrates a frontal view of idler carriage 504 and elongated shaft 502 in endoscopic device 501 from FIG. 5A. In FIG. 5B, cross-sectional frontal view 522 shows how the idler carriage 504 positions angled idlers 505, 506, 507, and 508 deliver the pull wires 518, 519, 520, and 521 to the elongated shaft 502 at a consistent and predictable location. In contrast to the previously disclosed embodiments, the angled idlers in endoscopic device 501 wrap and unwrap the pull wires at the same longitudinal position along the elongated shaft 502, which assists in maintaining a consistent takeoff angle for all of the pull wires regardless of the length of pull wire wrap around shaft 502.

As shown in FIG. 5A, the instrument base 503 also incorporates a pair of rotating structures 510 and 511. Rotating structures 510 and 511 comprise two concentrically-aligned, co-radial spools, such as spools 512, 513 from rotating structure 510, and spools 514, 515 from rotating structure 511. The rotating structures 510 and 511 incorporate output shafts 516 and 517 that interface with robotic drive and control mechanisms. Given that spools 512 and 513 and spools 514 and 515 are co-radial, output shaft 516 and 517 each includes both an inner and outer sub-shaft that drives each spool per rotating structure.

In some embodiments, the output shafts may be replaced by "female" or receiving interfaces rather "male" or protruding interfaces. As shown in isometric view 500, pull wires 518, 519, 520, and 521 are coiled around spools 512, 513, 514, and 515 and run around the angled idlers 505, 506, 507, and 508 before spiraling around the elongated shaft 502.

Figure 5C:
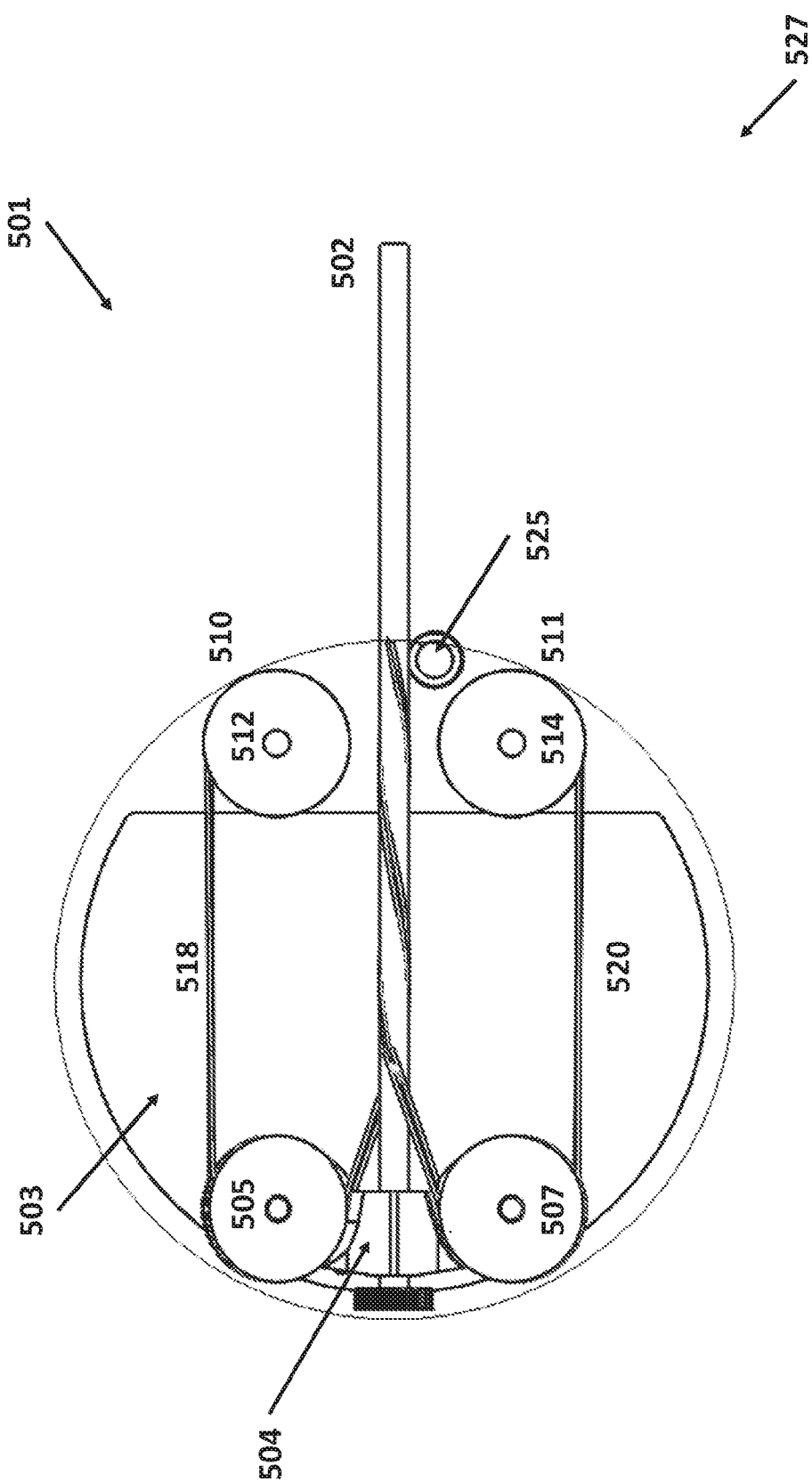
FIG. 5C illustrates a top view that shows the configuration of the key components of endoscopic device 501 from FIG. 5A.

FIG. 5C illustrates a top view that shows the configuration of the key components of endoscopic device 501 from FIG. 5A. Specifically, top view 527 provides a view of the direct alignment of a tangential path between rotation structures 510 and 511 and angled idlers 505 and 507 on idler carriage 504. As shown in top view 527, pull wire 518 is coiled around spool 512 and fed around angled idler 505 before spiraling around elongated shaft 502. The tangential path of the pull wires 518, 520 around the idlers 505, 507 are aligned with the spools 512, 514. Thus, in some embodiments, the spools 513 and 515 are also aligned with the angled idlers 506 and 508 in order for pull wires 519 and 521 to have a direct transmission path between the spools and idlers. In some embodiments, the idlers 505, 506, 507, and 508 may rotate in order to reduce friction as the pull wires 518, 519, 520, and 521 wind around them. While the idlers 505, 506, 507, and 508 operate similar to rotatable spools or pulleys, other embodiments may use other types of redirect members, such as surfaces.

Maintaining a consistent wrapping and unwrapping position and takeoff angle helps ensure that the pull wires spiral around the elongated shaft 502 at a consistent helical pitch. The consistency in the helical pitch greatly increases the ability of the robotic system to control and predict the tension on the pull wires.

In some embodiments, the elongated shaft 502 may be fixedly coupled to a concentric internal shaft that solely resides within the instrument base and is designed for wrapping pull wires around itself. Rolling the internal shaft would effectively roll the elongated shaft while potentially providing other advantages. For example, a distinct internal shaft may be adopted in order to take advantage of different coefficients of friction, different pull wire guiding features, such as grooves or lumens, different diameters, and potentially reduced manufacturing complexity and/or costs.

Angular motion from the robotic interface may create, for example, rotational motion in spool 512 through output shaft 516. Rotational motion in spool 512 may then exert compressive tension in pull wire 518. Tension in pull wire 518 may be carried around angled idler 505 and exerted on the pull wire 518 as it wraps onto elongated shaft 502. Where the pull wires 518 are fixedly coupled to the distal end of the shaft 502, the transmission of the compressive tension along pull wire 518 may then articulate the shaft 502. Thus, the angular motion in the robotic interface may generate articulation in shaft 502.

The instrument base 503 also comprises a lead screw 509 that runs parallel to the elongated shaft 502. Rotation of lead screw 509 is operated by a right angle gear transmission 525, which is visible in isometric view 500 from FIG. 5A. Rotational force in right angle gear transmission 525 originates from lead screw output shaft 526 which interfaces with external robotic drive and control mechanisms. Thus, angular motion in the robotic interface may rotate lead screw output shaft 526 to generate angular motion that ultimately rotates lead screw 509. As with the rotational structures 510 and 511, rotation motion from the robotic interface may also be transmitted to right angle gear transmission 525 using "female" or receiving connectors, rather than lead screw output shaft 526, which is considered a "male" connector.

FIG. 5D illustrates a rear view of the elongated shaft and idler carriage from FIGS. 5A, 5B, and 5C. As shown in rear view 524 from FIG. 5D, lead screw 509 is operatively coupled to elongated shaft 502 through a shaft transmission gear 523. Shaft transmission gear 523 transmits angular motion from the lead screw 509 that rotates the shaft 502. In different embodiments, the shaft transmission gear 523 may be selected from various gear and transmission ratios to ensure the desired rotational motion in the elongated shaft 502 relative to the lead screw 509.

The combination of the shaft 502, lead screw 509, and the idler carriage 504 manages the linear translation of the idler carriage 504 (and thus angled idlers 505, 506, 507, and 508) that helps preserve the helical pitch of the pull wires when rolling of shaft 502. In practice, elongated shaft 502 rotates at a relative speed determined by the angular motion transmitted by shaft transmission gear 523 which is proportional to the rotation of lead screw 509. As the lead screw 509 rotates itself and the elongated shaft 502, the idler carriage 504 acts as a nut on lead screw 509. This "lead screw nut" engagement advances the idler carriage 504 at a rate proportional to the rotation of both the lead screw 509 and elongated shaft 502. Thus, idler carriage 504 translates along the lead screw 509 while sliding freely along the elongated shaft 502 as lead screw 509 rotates itself and elongated shaft 502. The pitch and angle of the thread on lead screw 509 determines the direction and speed at which the idler carriage 504 advances relative to the elongated shaft 502. Similarly, the rate of rotation of elongated shaft 502 is dependent on at least the size of shaft transmission gear 523. Accordingly, careful calibration and selection of those components ensures that they properly coordinate in unison in order to keep consistent the helical pitch and angle of the pull wires about the elongated shaft 502.

Given that the idler carriage 504 translates along the length of the shaft 502 during roll operations, the length and pitch of the lead screw 509 may limit the number of elongated shaft roll revolutions allowed by the device 501. Consequently, longer devices with longer lead screws will generally allow greater shaft roll revolutions than shorter devices with shorter lead screws. Accordingly there may be a longer instrument base 503 to accommodate more rotations from a given lead screw with a specific pitch. Moreover, since wraps around the shaft 502 are directly proportional to the revolutions the shaft 502 may roll, an excessive number of wraps may heavily influence friction. Alternatively, a tighter pitch or steeper angle in the grade of the lead screw 509 may also affect roll revolutions and thus the length of the instrument base.

Figure 6B:
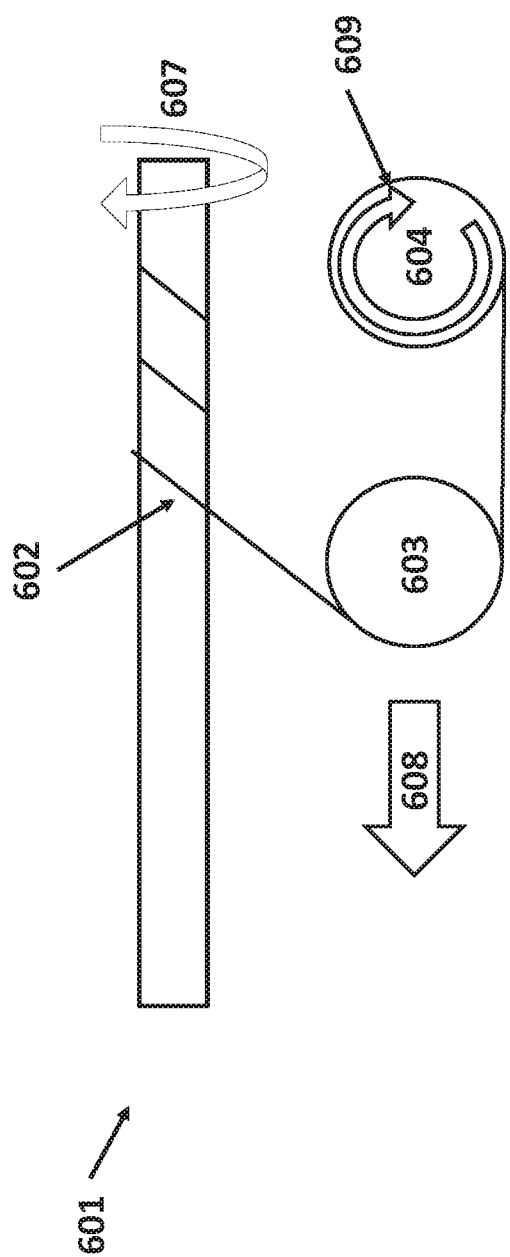
FIG. 6B illustrates how the elongated shaft, pull wire, angled idler, and spool components from FIG. 6A maintain a consistent helical pitch when rolling the elongated shaft clockwise.
Figure 6C:
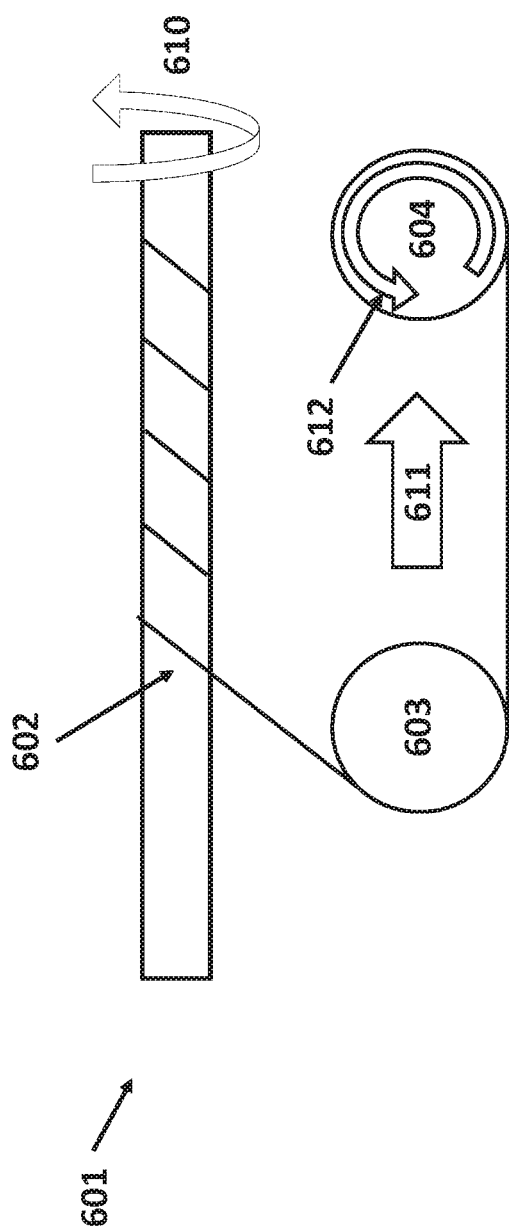
FIG. 6C illustrates how the elongated shaft, pull wire, angled idler, and spool from FIGS. 6A, 6B maintain a consistent helical pitch when rolling the elongated shaft counter-clockwise.

FIGS. 6A-6C illustrates roll and articulation operations of endoscopic device 501 with respect to a single pull wire, single angled idler, and single spool. Specifically, FIG. 6A illustrates how a single pull wire may be tensioned in order to generate articulation in the elongated shaft. As shown in isolated top view 600, exemplar elongated shaft 601 may already be wrapped with a single pull wire 602. Similar to the earlier embodiments, pull wire 602 may be directed to spiral onto a portion of the elongated shaft 601 by angled idler 603. The pull wire 602 may also be controlled via spool 604, whose rotational motion may generate compressive force along the length of the pull wire 602. Thus, in order to tension pull wire 602 and articulate the distal tip of shaft 601, shaft 601 and idler 603 remain static while spool 604 rotates in the direction indicated by arrow 606 to create compression tension along pull wire 602 in the direction indicated by arrow 605. That "pulling" force is then transferred along the length of pull wire around idler 603, along shaft 601 until reaching the distal tip, where the pull wire 602 is fixedly coupled. As the pull wire 602 is fixedly coupled to the end of the distal end of the elongated shaft 601, compressive tension results in bending or articulating of the elongated shaft 601.

FIG. 6B illustrates how the elongated shaft, pull wire, angled idler, and spool components from FIG. 6A maintain a consistent helical pitch when rolling the elongated shaft clockwise. In order to roll the elongated shaft 601, the angled idler 603 may be moved simultaneously to maintain a consistent takeoff angle in the pull wire 602. When rolling the elongated shaft 601 in the clockwise direction indicated by arrow 607, in order to maintain the helical pitch, the angled idler 603 may be translated longitudinally relative to the shaft 601 in the direction indicated by arrow 608. Translating the idler 603 while shaft 601 rotates ensures that the pull wire 602 is wrapped around shaft 601 with a consistent helix by ensuring that the pull wire 602 always has the same takeoff angle from angled idler 603. Put differently, translating the idler 603 in the direction of arrow 608 ensures that the pull wire 602 is "wrapped" around unwrapped portions of the shaft 601 at an even pitch, rather than wrapping in an uneven pitch or even on already-wrapped portions of the shaft 601. Due to the translation of the idler tension in the pull wire 602 requires that the spool 604 be rotated in direction indicated by arrow 609 in order to allow additional length of the pull wire 602 to be wrapped around shaft 601 at a consistent takeoff angle. In effect, the spool 604 must unwrap additional length of the pull wire 602 from itself in order to accommodate the additional wrapping of the pull wire 602 around the shaft 601 and the translation of the idler 603. The rate at which idler 603 advances in direction 608 relative to the rotation of 601 in direction 607 ensures that pull wire 602 is always encounters shaft 601 at the same takeoff angle, which maintains a consistent helical pitch and angle around the shaft 601.

FIG. 6C illustrates how the elongated shaft, pull wire, angled idler, and spool from FIGS. 6A, 6B maintain a consistent helical pitch when rolling the elongated shaft counter-clockwise. When rolling the elongated shaft 601 in the counter-clockwise direction indicated by arrow 610, in order to maintain the helical pitch, the angled idler 603 may be translated longitudinally relative to the shaft 601 in the direction indicated by arrow 611. Translating the idler 603 while shaft 601 rotates ensures that the pull wire 602 has the same takeoff angle as it unwraps from shaft 601. Put differently, translating the idler 603 in the direction of arrow 611 ensures that the pull wire 602 is "unwrapped" with the same takeoff angle from the shaft 601 preserving the helical pitch and angle of the pull wire 602 still wrapped about the shaft 601. Due to the translation of the idler 603, the formation of slack in the pull wire 602 requires that the spool 604 be rotated in direction indicated by arrow 612 in order to collect the loose length of pull wire 602. In effect, the spool 604 must wrap and collect additional length of the pull wire 602 to accommodate the "unwrapping" of the pull wire 602 from the shaft 601 and the translation of the idler 603. The angle of the idler 603 ensures that pull wire 602 is always unwrapped from the shaft 601 at the same point, helping ensure a consistent helical pitch and angle about shaft 601.

The embodiments in FIGS. 5A-5D, 6A-6C enable three-degrees of freedom at the tip of a flexible, articulating device while maintaining a static instrument base (503). By constraining the pull wire helical pitch on the elongated shaft during roll operations, tension variability is minimized and articulation controls are simplified. Furthermore, the design allows for functional adjustments and fine-tuning of features, such as shaft revolutions and relative carriage speed, merely by altering the features of the lead screw and transmission gears. Different configurations of helical wire pitches and the number of revolutions can be attained simply by varying the length of the lead screw, pitch of the threads, and its associated drivetrain to the main shaft. Moreover, the compact design also allows for electronics (such as circuit board 527 in FIG. 5A) and other internal features to be placed within the instrument base.

The embodiments in FIGS. 5A-5D, 6A-6C allow the ability to rotate or "roll" the flexible shaft after a long journey through a tortuous path in the patient's anatomy. For example, after traversing through a long and tortuous path, endoscopic device 501 may articulate elongated shaft 502 and roll elongated shaft 502 in order to reach to an operative site. In some circumstances, it may be useful to first roll elongated shaft 502 and then articulate elongated shaft 502 in order to reach certain locations with the patient's anatomy. Use of roll may also provide improved access to operative sites where robotically-driven articulation may be insufficient and ineffective, a circumstance that may occur as a result of traversing through tortuous paths.

In addition to improved reach, the disclosed embodiments may also enable roll to reduce braking static friction when traversing through a tortuous path. For example, rolling elongated shaft 502 while simultaneously extending into an anatomical lumen may reduce friction caused from contact with the lumen walls. Furthermore, rolling the elongated shaft 502 may also reduce friction caused by contact at anatomical transitions.

In practice, rolling and subsequently articulating endoscopic device 501 within an anatomical lumen involves several mechanical steps. For example, the instrument interface would first rotate lead screw output shaft 526 in order to rotate right angle gear transmission 525. In response to rotating right angle gear transmission 525, lead screw 509 would rotate. The rotation of the lead screw 509 would result in the motion of several components within the instrument base 503. Firstly, the rotation of the lead screw 509 would transmit angular motion to shaft transmission gear 523 which would cause shaft 502 to rotate.

Secondly, rotation of the lead screw 509 would also cause idler carriage 504 to laterally move along the shaft 502. Depending on the direction of rotation and the thread of lead screw 509, the idler carriage 504 may either move forward towards the distal tip of the elongated shaft 502 or back towards the proximal end of the elongated shaft 502.

The roll of elongated shaft 502 creates tension on pull wires 518, 519, 520, 521. To compensate and alleviate the tension, instrument interface would rotate output shafts 516 and 517 (and their associated concentrically-aligned sub-shafts) in order to reduce tension in the pull wires as explained in FIGS. 6B and 6C. Once the roll is complete, the tension-compensation process may terminate. After rotating the shaft 502, the distal tip of the shaft 502 may then be articulated in order to reach the desired operative site. Tensioning the appropriate pull wire in order to articulate may be executed using the technique described in FIG. 6A.

The aforementioned embodiments of the present invention may be designed to interface with robotics platform such as those disclosed in the aforementioned patent applications that are incorporated by reference. For example, the embodiments in FIGS. 5A-5D, 6A-6D may be configured to be driven by an instrument drive mechanism or an instrument device manipulator that is attached to the distal end of a robotic arm through a sterile interface, such as a drape. As part of a larger robotics system, robotic control signals may be communicated from a remotely-located user interface, down the robotic arm, and to the instrument device manipulator to control the instrument or tool.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A method of operating a medical tool, the method comprising:
    rotating an elongate shaft of the medical tool with a drive output of a robotic system;
    wrapping at least one pull wire over the elongate shaft at a predetermined angle as the elongate shaft rotates;
    tensioning the at least one pull wire to articulate at least a portion of the elongate shaft; and
    maintaining the predetermined angle of the at least one pull wire as the elongate shaft rotates or the at least one pull wire is tensioned,
    wherein maintaining the predetermined angle comprises providing at least one spooling element coupled to the at least one pull wire, the at least one spooling element wrapping or un-wrapping the at least one pull wire as the elongate shaft rotates.

2. The method of claim 1, where the at least one spooling element comprises at least one articulating shaft spooling the at least one pull wire.

3. The method of claim 2, further comprising wrapping or un-wrapping the at least one pull wire from the at least one articulating shaft at a same predetermined angle the at least one pull wire is wrapped around the elongate shaft.

4. The method of claim 3, wherein wrapping or un-wrapping the at least one pull wire from the at least one articulating shaft at the same predetermined angle comprises rotating the at least one articulating shaft in a same direction as the elongate shaft rotates in.

5. The method of claim 2, wherein tensioning the at least one pull wire to articulate at least the portion of the elongate shaft comprises rotating the at least one articulating shaft in coordination with the elongate shaft.

6. The method of claim 1, wherein the at least one spooling element comprises at least one idler spooling the at least one pull wire.

7. The method of claim 6, wherein maintaining the predetermined angle of the at least one pull wire comprises fixing a positon of the at least one idler relative to the elongate shaft.

8. The method of claim 6, wherein the at least one spooling element further comprises at least one rotating structure, and wherein each pull wire is configured to coil around both an individual idler and a complementary individual rotating structure.

9. The method of claim 8, wherein tensioning the at least one pull wire to articulate at least the portion of the elongate shaft comprises rotating the at least one rotating structure in coordination with the elongate shaft.

10. The method of claim 1, further comprising coupling the at least one spooling element to the drive output of the robotic system.

11. A method of operating a medical tool, the method comprising:
   rotating an elongate shaft of the medical tool with a drive output of a robotic system, wherein rotating the elongate shaft comprises coupling an instrument base coupled to a proximal end of the elongate shaft to the drive output of the robotic system;
   wrapping at least one pull wire over the elongate shaft at a predetermined angle as the elongate shaft rotates;
   tensioning the at least one pull wire to articulate at least a portion of the elongate shaft; and
   maintaining the predetermined angle of the at least one pull wire as the elongate shaft rotates or the at least one pull wire is tensioned.

12. A method of operating a medical tool, the method comprising:
   rotating an elongate shaft of the medical tool with a drive output of a robotic system;
   wrapping at least one pull wire over the elongate shaft at a predetermined angle as the elongate shaft rotates;
   tensioning the at least one pull wire to articulate at least a portion of the elongate shaft; and
   maintaining the predetermined angle of the at least one pull wire as the elongate shaft rotates or the at least one pull wire is tensioned, wherein the predetermined angle comprises a predetermined helical pitch and angle.

13. The method of claim 12, wherein maintaining the predetermined angle comprises providing at least one spooling element coupled to the at least one pull wire, the at least one spooling element wrapping or un-wrapping the at least one pull wire as the elongate shaft rotates.

14. The method of claim 13, where the at least one spooling element comprises at least one articulating shaft spooling the at least one pull wire.

15. The method of claim 14, further comprising wrapping or un-wrapping the at least one pull wire from the at least one articulating shaft at a same predetermined angle the at least one pull wire is wrapped around the elongate shaft.

16. The method of claim 15, wherein wrapping or un-wrapping the at least one pull wire from the at least one articulating shaft at the same predetermined angle comprises rotating the at least one articulating shaft in a same direction as the elongate shaft rotates in.

17. The method of claim 14, wherein tensioning the at least one pull wire to articulate at least the portion of the elongate shaft comprises rotating the at least one articulating shaft in coordination with the elongate shaft.

18. The method of claim 13, wherein the at least one spooling element comprises at least one idler spooling the at least one pull wire.

19. The method of claim 18, wherein maintaining the predetermined angle of the at least one pull wire comprises fixing a positon of the at least one idler relative to the elongate shaft.

20. The method of claim 18, wherein the at least one spooling element further comprises at least one rotating structure, and wherein each pull wire is configured to coil around both an individual idler and a complementary individual rotating structure.

21. The method of claim 20, wherein tensioning the at least one pull wire to articulate at least the portion of the elongate shaft comprises rotating the at least one rotating structure in coordination with the elongate shaft.

22. The method of claim 11, wherein maintaining the predetermined angle comprises providing at least one spooling element coupled to the at least one pull wire, the at least one spooling element wrapping or un-wrapping the at least one pull wire as the elongate shaft rotates.

23. The method of claim 22, where the at least one spooling element comprises at least one articulating shaft spooling the at least one pull wire.

24. The method of claim 23, further comprising wrapping or un-wrapping the at least one pull wire from the at least one articulating shaft at a same predetermined angle the at least one pull wire is wrapped around the elongate shaft.

25. The method of claim 24, wherein wrapping or un-wrapping the at least one pull wire from the at least one articulating shaft at the same predetermined angle comprises rotating the at least one articulating shaft in a same direction as the elongate shaft rotates in.

26. The method of claim 23, wherein tensioning the at least one pull wire to articulate at least the portion of the elongate shaft comprises rotating the at least one articulating shaft in coordination with the elongate shaft.

27. The method of claim 22, wherein the at least one spooling element comprises at least one idler spooling the at least one pull wire.

28. The method of claim 27, wherein maintaining the predetermined angle of the at least one pull wire comprises fixing a positon of the at least one idler relative to the elongate shaft.

29. The method of claim 27, wherein the at least one spooling element further comprises at least one rotating structure, and wherein each pull wire is configured to coil around both an individual idler and a complementary individual rotating structure.

30. The method of claim 29, wherein tensioning the at least one pull wire to articulate at least the portion of the elongate shaft comprises rotating the at least one rotating structure in coordination with the elongate shaft.

* * * * *